US012661325B2

(12) United States Patent (10) Patent No.: US 12,661,325 B2
Suzuki et al. (45) Date of Patent: Jun. 23, 2026

(54) FILM COATED TABLET

(71) Applicant: KIRIN HOLDINGS KABUSHIKI KAISHA, Tokyo (JP)

(72) Inventors: Yasuhiro Suzuki, Tokyo (JP); Toshiki Yamaoka, Tokyo (JP); Yohei Yamazoe, Tokyo (JP)

(73) Assignee: KIRIN HOLDINGS KABUSHIKI KAISHA, Tokyo (JP)

( * ) Notice: Subject to any disclaimer, the term of this patent is extended or adjusted under 35 U.S.C. 154(b) by 473 days.

(21) Appl. No.: 18/005,095

(22) PCT Filed: Jul. 13, 2021

(86) PCT No.: PCT/JP2021/026329
§ 371 (c)(1),
(2) Date: Jan. 11, 2023

(87) PCT Pub. No.: WO2022/014601
PCT Pub. Date: Jan. 20, 2022

(65) Prior Publication Data
US 2023/0263735 A1 Aug. 24, 2023

(30) Foreign Application Priority Data

Jul. 13, 2020 (JP) ................................ 2020-120267

(51) Int. Cl.
| *A61K 9/28* | (2006.01) |
| *A23L 29/00* | (2016.01) |
| *A23L 29/256* | (2016.01) |
| *A23L 29/269* | (2016.01) |

(52) U.S. Cl.
CPC .......... *A61K 9/2886* (2013.01); *A23L 29/015* (2016.08); *A23L 29/256* (2016.08); *A23L 29/27* (2016.08); *A61K 9/2813* (2013.01); *A61K 9/286* (2013.01); *A61K 9/2866* (2013.01)

(58) Field of Classification Search
None
See application file for complete search history.

(56) References Cited

U.S. PATENT DOCUMENTS

| 5,334,393 | A | * | 8/1994 | Bougaret | ............. | A61K 9/2054 |
| | | | | | | 424/464 |
| 5,690,960 | A | * | 11/1997 | Bengtsson | ................ | A61P 1/04 |
| | | | | | | 424/494 |
| 2010/0255146 | A1 | | 10/2010 | Seko et al. | | |
| 2012/0082723 | A1 | * | 4/2012 | Kudou | ................ | A61K 31/5383 |
| | | | | | | 424/479 |
| 2013/0017245 | A1 | | 1/2013 | Takano | | |
| 2015/0079171 | A1 | | 3/2015 | Kudou et al. | | |
| 2016/0220472 | A1 | * | 8/2016 | Wang | .................. | A61K 8/8152 |
| 2018/0371212 | A1 | | 12/2018 | Seko et al. | | |
| 2020/0214987 | A1 | * | 7/2020 | Oliveira Varum | ... | A61K 9/2846 |
| 2020/0330347 | A1 | * | 10/2020 | Wlaschin | ................. | A61K 8/41 |

FOREIGN PATENT DOCUMENTS

| CN | 102811712 | A | | 12/2012 |
| EP | 0973527 | | * | 1/2000 |
| EP | 1095651 | A2 | | 5/2001 |
| EP | 2067409 | A1 | | 6/2009 |
| EP | 2550961 | A1 | | 1/2013 |
| JP | H07-033659 | A | | 2/1995 |
| JP | 2001-131059 | A | | 5/2001 |
| JP | 2002-275054 | A | | 9/2002 |
| JP | 2008-043249 | A | | 2/2008 |
| WO | WO 1994/002140 | A1 | | 2/1994 |
| WO | 2011/118453 | A1 | | 9/2011 |
| WO | WO 2011/125798 | A1 | | 10/2011 |
| WO | WO 2016/035756 | A1 | | 3/2016 |

OTHER PUBLICATIONS

Dahl et al. "Influence of physico-chemical properties of hydroxypropyl methyl methylcellulose on naproxen release from sustained release matrix" abstract 1990.*
Methocel® K100LV.*
Japan Patent Office, International Search Report in International Patent Application No. PCT/JP2021/026329 (Sep. 21, 2021).
European Patent Office, Extended European Search Report in European Patent Application No. 21842850.6 (Jul. 12, 2024).
Japan Patent Office, Written Opinion of the International Searching Authority in International Patent Application No. PCT/JP2021/026329 (Sep. 21, 2021).
Hu, "Pharmaceutical Adjuvants: Production and Application of Film Coating Premix" Chinese Medical Technology Press, p. 24 (2014).
Zhang et al., "Effect of Electrolyte on the Rheological Behaviors of Sodium Alginate Solutions," Journal of Qingdao University (Natural Science Edition), 26(2): 57-61 (2013) [see English abstract thereof and English translation of CNIPA Office Action dated Nov. 29, 2024 for Chinese Patent Application No. 202180061278.8].
China National Intellectual Property Administration, Office Action in Chinese Patent Application No. 202180061278.8 (Nov. 29, 2024).
Hastoris et al., "Food Additives," p. 141, Chinese Agricultural University Press, 3rd Edition (2016).
Duan (ed.), "Natural Polymeric Materials," pp. 230-231, Warch Scientific University Press, 1st Edition (2016).

(Continued)

*Primary Examiner* — Danah Al-Awadi
(74) *Attorney, Agent, or Firm* — Leydig, Voit & Mayer, Ltd.

(57) ABSTRACT

An object of the present invention is to provide a film coated tablet that has an excellent tablet slipperiness in an oral cavity and prevents delay in disintegration time of an uncoated tablet. The present invention provides a film coated tablet including a tablet, a first film layer that coats the tablet and contains an inorganic salt, and a second film layer that coats the tablet coated with the first film layer and contains a thickener, and a film coated tablet including a tablet, a first film layer that coats the tablet, and a second film layer that coats an outside of the first film layer and contains a thickener, in which the first film layer contains an inorganic salt, and the inorganic salt reduces a viscosity of the thickener contained in the second film layer.

18 Claims, 1 Drawing Sheet

(56)           References Cited

OTHER PUBLICATIONS

National Association of Science and Technology (ed.), "Pharmacology Development Report 2008-2009," pp. 179-180, Chinese Science and Technology Press, 1st Edition (2009).
China National Intellectual Property Administration, Office Action in Chinese Patent Application No. 202180061278.8 (May 13, 2025).
China National Intellectual Property Administration, Office Action in Chinese Patent Application No. 202180061278.8 (Jul. 30, 2025).
Japan Patent Office, Office Action in Japanese Patent Application No. 2022-536397 (Jul. 8, 2025).

* cited by examiner

FILM COATED TABLET

TECHNICAL FIELD

The present invention relates to a film coated tablet. More specifically, the present invention relates to a film coated tablet used in fields of pharmaceuticals and health foods.

BACKGROUND ART

Oral administration of a tablet and the like is a common method for administering and ingesting a pharmaceutically active ingredient, a nutritional supplement active ingredient, a food ingredient, etc. Tablets are excellent in handleability, dosing property, and portability, and is the most commercially available dosage form of oral administration preparations. However, in the medical field, it is sometimes necessary to take many tablets or large tablets. In addition, in the field of health foods, a tablet form is widely used as a dosage form for nutritional supplements and foods with functional claims, and a plurality of tablets may be taken at once. Further, it may be difficult for the elderly, children, and patients with impaired swallowing function to take tablets. Thus, taking a plurality of tablets or large tablets is a burden for various patients and consumers. Therefore, tablets that are easy to swallow are desired.

As a tablet that is easy to swallow, for example, Patent Literature 1 discloses an easily administrable solid preparation in which by blending a thickener, a binder, and a sugar alcohol in a coating layer, a slimy feeling or adhesion feeling to an oral cavity upon administration is prevented. In addition, Patent Literature 2 discloses an easily administrable solid preparation in a mini-tablet form in which by blending a plurality of thickeners and a polyvalent metal compound in a coating layer, a surface layer of a tablet rapidly turns into a gel upon administration, thereby increasing a viscosity and making it easier to slip on a mucosa.

CITATION LIST

Patent Literature

Patent Literature 1: JP2002-275054A
Patent Literature 2: WO2011/125798

SUMMARY OF INVENTION

Technical Problem

A thickener is a component for improving a slipperiness of a tablet. On the other hand, the thickener is also a component used in sustained-release preparations that prevents or controls dissolution of an active ingredient, such as delaying a disintegration time of a tablet. Therefore, there is concern that in tablets with a thickener blended in a film layer so as to make the tablets easier to swallow, release of the active ingredient is delayed due to the disintegration time in a gastrointestinal tract being delayed, and an original efficacy and effect cannot be sufficiently exerted. In addition, there is a problem that a dissolution property of the active ingredient is decreased depending on a drug contained in the tablet and a composition of the film layer. Therefore, there is a demand for a film layer that does not affect a disintegration time of an uncoated tablet in a gastrointestinal tract while maintaining a slipperiness of a tablet.

A problem to be solved by the present invention is to provide a film coated tablet that has an excellent tablet slipperiness in an oral cavity and prevents delay in disintegration time of an uncoated tablet.

Solution to Problem

As a result of intensive studies on the above-described problem, it is found that a film coated tablet having an excellent swallowability and an improved tablet disintegration time can be prepared by a tablet, containing an inorganic salt in a first film layer coating the tablet, and containing a thickener in a second film layer that is an outer layer, and the present invention is made based on such findings.

That is, the following (1) to (7) are provided as methods for solving the above-described problem.

(1) A film coated tablet, including:
a tablet;
a first film layer that coats the tablet and contains an inorganic salt; and
a second film layer that coats the tablet coated with the first film layer and contains a thickener.

(2) A film coated tablet, including:
a tablet;
a first film layer that coats the tablet; and
a second film layer that coats an outside of the first film layer and contains a thickener, in which
the first film layer contains an inorganic salt, and the inorganic salt reduces a viscosity of the thickener contained in the second film layer.

(3) A film coated tablet, including:
a tablet;
a first film layer that coats the tablet; and
a second film layer that coats an outside of the first film layer and contains a thickener, in which
the first film layer contains an inorganic salt and a water-soluble film base having a 2% by mass aqueous solution viscosity at 20° C. of 100 mPa·s or less.

(4) The film coated tablet according to any one of (1) to (3), in which
a content of the inorganic salt in the first film layer is 20 to 55% by mass, and
a content of the thickener in the second film layer is 20 to 40% by mass.

(5) The film coated tablet according to any one of (1) to (4), in which
the first film layer is 2 to 6 parts by mass per 100 parts by mass of an uncoated tablet, and
the second film layer is 2 to 4 parts by mass per 100 parts by mass of the uncoated tablet.

(6) The film coated tablet according to any one of (1) to (5), in which
the inorganic salt contained in the first film layer is a water-soluble inorganic salt.

(7) The film coated tablet according to any one of (1) to (5), in which
the inorganic salt contained in the first film layer is at least one selected from the group consisting of potassium phosphate, sodium hydrogen carbonate and sodium chloride, and
the thickener contained in the second film layer is at least one selected from the group consisting of sodium alginate and xanthan gum.

Advantageous Effects of Invention

According to the film coated tablet of the present invention, it is possible to provide a film coated tablet that has an improved tablet swallowability and prevents delay in disintegration time of a tablet in a gastrointestinal tract.

DESCRIPTION OF EMBODIMENTS

Hereinafter, embodiments of film coated tablets will be described in detail with reference to the drawings.

It should be noted that the film coated tablets described in the embodiments are merely exemplified to illustrate the film coated tablets, and are not limited thereto.

Figure 1:
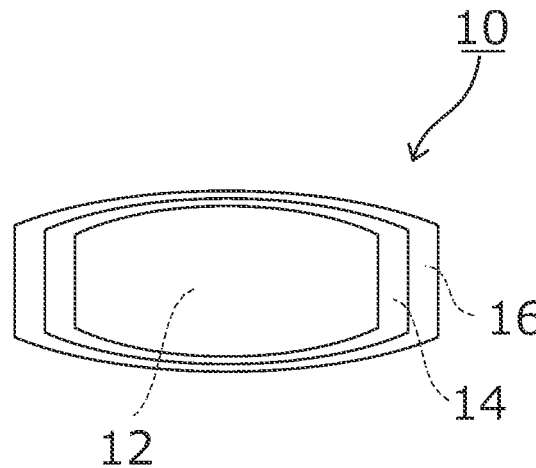
FIG. 1 is a schematic diagram illustrating a cross section of a film coated tablet.

FIG. 1 is a schematic diagram illustrating a cross section of a film coated tablet according to the present invention. As shown in FIG. 1, a film coated tablet 10 includes an uncoated tablet 12 containing an active ingredient having a desired efficacy and effect, a first film layer 14 as an inner layer coating an outside of the uncoated tablet 12, and a second film layer 16 as an outer layer coating an outside of the tablet coated with the first film layer.

A first aspect of the present invention is a film coated tablet including a tablet, a first film layer that coats the tablet and contains an inorganic salt, and a second film layer that coats the tablet coated with the first film layer and contains a thickener.

According to the film coated tablet of the first aspect of the present invention, when the second film layer comes into contact with water, a surface of the tablet exhibits a slipperiness, which facilitates swallowing of the tablet. Further, an effect of preventing delay in disintegration time of an uncoated tablet can be exerted by a function of the inorganic salt in the first film layer.

A second aspect of the present invention is a film coated tablet including a tablet, a first film layer that coats the tablet, and a second film layer that coats an outside of the first film layer and contains a thickener, in which the first film layer contains an inorganic salt, and the inorganic salt reduces a viscosity of the thickener contained in the second film layer.

According to the film coated tablet of the second aspect of the present invention, since the viscosity of the thickener in the outer layer can be reduced by a function of the inorganic salt contained in the first film layer, a tablet swallowability and an effect of preventing delay in disintegration time of an uncoated tablet can be exerted by facilitating penetration of water into the tablet.

A third aspect of the present invention is a film coated tablet including a tablet, a first film layer that coats the tablet, and a second film layer that coats an outside of the first film layer and contains a thickener, in which the first film layer contains an inorganic salt and a water-soluble film base having a 2% by mass aqueous solution viscosity at 20° C. of 100 mPa·s or less.

According to the film coated tablet of the third aspect of the present invention, by a function of the inorganic salt contained in the first film layer, an effect of shortening a disintegration time of an uncoated tablet can be exerted by rapid penetration of water into the tablet. In addition, dissolution of the first film layer is facilitated by containing a low-viscosity water-soluble film base in the first film layer. Further, since a viscosity of a liquid in which the first film layer is dissolved is low, penetration of water into the tablet can be facilitated.

In one aspect of the present invention, a film coated tablet contains an inorganic salt in a first film layer and a thickener in a second film layer. Thus, when the film coated tablet is taken, it is possible to exert an effect of first imparting a slipperiness to a surface of the tablet by the thickener in the second film layer in contact with water or saliva, and then preventing delay in disintegration time of the tablet in a gastrointestinal tract by a function of the inorganic salt in the first film layer. It should be noted that a plurality of film-coating layers may be provided inside the first film layer, between the first film layer and the second film layer, and outside the second film layer.

A shape of the tablet is not particularly limited, and examples thereof include round tablets, oval tablets, and flower-shaped tablets. In addition, the tablet can be provided with one or two dividing lines for dividing the tablet into two or four parts as necessary.

A size of the tablet is not particularly limited. For example, in a case of a round tablet, a diameter thereof is preferably 3 mm or more and 20 mm or less. A lower limit value thereof is more preferably 5 mm or more, still more preferably 7 mm or more, and particularly preferably 9 mm or more. On the other hand, an upper limit value thereof is more preferably 15 mm or less, and still more preferably 12 mm or less.

A thickness of the tablet is not particularly limited, and is preferably 2.0 mm or more and 10.0 mm or less, for example. A lower limit value thereof is more preferably 2.5 mm or more, still more preferably 3.0 mm or more, and particularly preferably 3.5 mm or more. On the other hand, an upper limit value thereof is more preferably 9.0 mm or less, still more preferably 8.0 mm or less, and particularly preferably 6.0 mm or less.

The tablet can be easily taken by setting the size and thickness of the tablet within the respective ranges.

A coating amount of the first film layer is not particularly limited, and is preferably, for example, 0.1 parts by mass or more and 20.0 parts by mass or less per 100 parts by mass of the uncoated tablet. A lower limit value thereof is more preferably 0.5 parts by mass or more, still more preferably 1.0 parts by mass or more, and particularly preferably 2.0 parts by mass or more. On the other hand, an upper limit value thereof is more preferably 15.0 parts by mass or less, still more preferably 10.0 parts by mass or less, still more preferably 8.0 parts by mass or less, and particularly preferably 6.0 parts by mass or less.

A coating amount of the second film layer is not particularly limited, and is preferably, for example, 0.1 parts by mass or more and 20.0 parts by mass or less per 100 parts by mass of the uncoated tablet. A lower limit value thereof is more preferably 0.5 parts by mass or more, still more preferably 1.0 parts by mass or more, and particularly preferably 2.0 parts by mass or more. On the other hand, an upper limit value thereof is more preferably 15.0 parts by mass or less, still more preferably 8.0 parts by mass or less, still more preferably 6.0 parts by mass or less, and particularly preferably 4.0 parts by mass or less.

As one aspect of the present invention, a film coated tablet is preferred in which the first film layer is 2 to 6 parts by mass per 100 parts by mass of the uncoated tablet, and the second film layer is 2 to 4 parts by mass per 100 parts by mass of the uncoated tablet. The tablet swallowability and the effect of preventing delay in disintegration time of the uncoated tablet can be further improved by controlling the coating amounts of the first film layer and the second film layer within the respective ranges.

As one aspect of the present invention, a mass ratio of the first film layer to the second film layer is preferably 1:1, preferably 2:1, and more preferably 3:1. The tablet swallowability and the effect of preventing delay in disintegration time of the uncoated tablet can be further improved by controlling the mass ratio of the first film layer to the second film layer within the range.

Each of thicknesses of the first film layer and the second film layer is not particularly limited, and is preferably 1 μm or more and 1000 μm or less, for example. A lower limit value thereof is more preferably 3 μm or more, still more preferably 5 μm or more, and particularly preferably 10 μm or more. On the other hand, an upper limit value thereof is more preferably 500 μm or less, still more preferably 200 μm or less, and particularly preferably 100 μm or less. It should be noted that a film thickness of a coating layer can be measured based on an image of a fracture surface of a preparation obtained by using a scanning electron microscope.

The swallowability and the effect of preventing delay in disintegration time of the uncoated tablet can be effectively imparted to the tablet by setting the weights and thicknesses of the first film layer and the second film layer within the respective ranges.

First Film Layer

The first film layer shortens the disintegration time of the tablet by containing an inorganic salt. First, components in the first film layer will be described in detail.

(Inorganic Salt)

The inorganic salt contained in the first film layer preferably reduces the viscosity of the thickener contained in the second film layer when the film coated tablet is taken, thereby shortening the disintegration time of the tablet. That is, the inorganic salt preferably reduces the viscosity of the thickener. In particular, the inorganic salt preferably reduces the viscosity of the thickener contained in the second film layer in a digestive organ after the film coated tablet is taken, thereby shortening the disintegration time of the tablet.

It should be noted that a characteristic that an inorganic salt reduces a viscosity of a thickener can be specified by, for example, determining whether a viscosity of an aqueous solution of the thickener is reduced when the inorganic salt is added to the aqueous solution.

As an example of a method for determining the characteristic that the inorganic salt reduces the viscosity of the thickener, for example, when a viscosity of a first thickener aqueous solution (20° C.) having a thickener concentration of 1% by mass is compared with a viscosity of a second thickener aqueous solution (20° C.) having a thickener concentration of 1% by mass and an inorganic salt concentration of 2% by mass, if the viscosity of the second thickener aqueous solution (20° C.) is lower, it can be specified that the inorganic salt reduces the viscosity of the thickener. It should be noted that the viscosity of the first or second thickener aqueous solution can be measured by the capillary viscometer method or the like prescribed in the 17th revised Japanese Pharmacopoeia.

The inorganic salt is preferably a water-soluble inorganic salt that is acceptable for use in pharmaceuticals and foods, and exhibits a solubility of 5 g or more per 100 g of water at 20° C. Examples of the inorganic salt include an inorganic compound obtained by substituting a hydrogen atom of a water-soluble inorganic acid with a metal.

Since the inorganic salt contained in the first film layer is water-soluble, the inorganic salt contained in the first film layer dissolves in water and reacts with the thickener contained in the second film layer to reduce the viscosity of the thickener, and thus the effect of preventing delay in disintegration time of the uncoated tablet can be further improved.

Specific examples of the inorganic salt include potassium phosphate (dipotassium phosphate), sodium phosphate (monosodium phosphate), calcium phosphate, potassium hydrogen phosphate (potassium dihydrogen phosphate), sodium hydrogen phosphate, calcium hydrogen phosphate, potassium carbonate, sodium carbonate, calcium carbonate, potassium hydrogen carbonate, sodium hydrogen carbonate, calcium hydrogen carbonate, potassium chloride, sodium chloride, and calcium chloride. Preferred inorganic salts are potassium phosphate, sodium hydrogen carbonate and sodium chloride from the viewpoint of being excellent in shortening the disintegration time of the tablet. In addition, these inorganic salts may be blended alone or in combination of two or more thereof.

It should be noted that when a carbonate-based inorganic salt (for example, potassium carbonate, sodium carbonate, calcium carbonate, potassium hydrogen carbonate, sodium hydrogen carbonate, and calcium hydrogen carbonate) is used in the first film layer, in order to improve a stability, it is preferred not to add an organic acid to the first film layer.

A content of the inorganic salt in the first film layer is not particularly limited, and is preferably, for example, 10% by mass or more and 60% by mass or less with respect to the mass of the first film layer. A lower limit value thereof is more preferably 13% by mass or more, still more preferably 15% by mass or more, and particularly preferably 20% by mass or more. On the other hand, an upper limit value thereof is more preferably 57% by mass or less, still more preferably 56% by mass or less, and particularly preferably 55% by mass or less. An effect of shortening the disintegration time of the tablet can be significantly improved by setting the content of the inorganic salt in the first film layer within the range.

(Water-Soluble Film Base of First Film Layer)

The water-soluble film base is a base for forming a film containing an inorganic salt, and is not particularly limited as long as it is acceptable for uses such as pharmaceuticals and foods. Examples thereof include cellulose derivatives, synthetic resins, and polysaccharides.

A viscosity of the water-soluble film base is preferably low. For example, the 2% by mass aqueous solution viscosity at 20° C. thereof is preferably 0.1 mPa·s or more and 100 mPa·s or less. A lower limit value thereof is more preferably 1 mPa·s or more, still more preferably 2 mPa·s or more, and particularly preferably 3 mPa·s or more. On the other hand, an upper limit value thereof is more preferably 45 mPa s or less, still more preferably 40 mPa·s or less, and particularly preferably 35 mPa·s or less. It should be noted that the viscosity of the water-soluble film base can be measured by the capillary viscometer method or the like prescribed in the 17th revised Japanese Pharmacopoeia.

Specific examples of the water-soluble film base include hydroxypropyl methylcellulose (2% by mass aqueous solution viscosity at 20° C. is 15 mPa·s or less), hydroxypropylcellulose (2% by mass aqueous solution viscosity at 20° C. is 10 mPa·s or less), polyvinyl alcohol (4% by mass aqueous solution viscosity at 20° C. is 6 mPa·s or less), polyvinylpyrrolidone (average molecular weight of 40,000 or less), methylcellulose (2% by mass aqueous solution viscosity at 20° C. is 15 mPa·s or less), and pullulan (10% by mass aqueous solution viscosity at 30° C. is 15 to 180 mPa s).

Preferred water-soluble film bases are hydroxypropyl methylcellulose and hydroxypropylcellulose from the viewpoint of being excellent in easy availability and ease of coating. In addition, these water-soluble film bases may be blended alone or in combination of two or more thereof.

A content of the water-soluble film base in the first film layer is not particularly limited, and is preferably, for example, 30% by mass or more and 80% by mass or less with respect to the mass of the first film layer. A lower limit value thereof is more preferably 33% by mass or more, still more preferably 35% by mass or more, and particularly preferably 40% by mass or more. On the other hand, an upper limit value thereof is more preferably 77% by mass or less, still more preferably 75% by mass or less, and particularly preferably 74% by mass or less. A tablet having an excellent coating property can be obtained by setting the content of the water-soluble film base in the first film layer within the range.

(Other Components)

In addition to the inorganic salt and the water-soluble film base, the first film layer may contain other components as necessary. Specific examples of components to be added include plasticizers, sweeteners, flavoring agents, colorants, and photoprotective agents.

It should be noted that in order to maintain a function of the first film layer of shortening the disintegration time of the tablet, it is preferred that a thickener that reacts with the inorganic salt contained in the first film layer to form a gel is not blended in the first film layer. In addition, it is more preferred that a thickener is not blended in the first film layer. By not blending a thickener, an effect of facilitating the dissolution of the first film layer and facilitating an action of the inorganic salt contained in the first film layer on the second film layer is achieved. It should be noted that the thickener will be described in the section of the second film layer.

By adding a plasticizer to the first film layer, a flexibility and elasticity of a composition for coating the uncoated tablet can be adjusted, and a coating performance can be improved. The plasticizer imparts the flexibility and elasticity of the composition, and is not particularly limited as long as it is acceptable for uses such as pharmaceuticals and foods Examples of the plasticizer include polyethers, polyhydric alcohols, esters, organic acids, and vegetable oils.

Specific examples of the plasticizer include polyethylene glycol, polypropylene glycol, glycerin, glycerol, polyol, triethyl citrate, acetylated monoglyceride, butyl phthalyl butyl glycolate, dibutyl tartrate, propylene glycol, glycerol monostearate, tripropioin, diacetin, citric acid, medium chain fatty acid oils, and rapeseed oils.

In addition, a molecular weight of the polyethylene glycol is preferably, for example, 4,000 or more and 20,000 or less. Specifically, examples of the polyethylene glycol include PEG6000 and PEG8000. In addition, these plasticizers may be blended alone or in combination of two or more thereof.

By adding a sweetener to the first film layer, the tablet can be sweetened to make it easier to take. The sweetener imparts a sweet taste to the tablet, and is not particularly limited as long as it is acceptable for uses such as pharmaceuticals and foods. Examples of the sweetener include natural sweeteners and artificial sweeteners.

Specific examples of the sweetener include erythritol, sorbitol, aspartame, acesulfame potassium, stevia, sucralose, glycyrrhizic acid, thaumatin, saccharin, and saccharin sodium. In addition, these sweeteners may be blended alone or in combination of two or more thereof.

By adding a flavoring agent to the first film layer, the tablet can be made easier to take. The flavoring agent improves an organoleptic sensation of the tablet in the oral cavity, and is not particularly limited as long as it is acceptable for uses such as pharmaceuticals and foods. Examples of the flavoring agent include natural vegetable oils and aldehyde compounds.

Specifically, examples of the flavoring agent include spearmint oils, peppermint oils, cinnamon oils, fruit essences, benzaldehyde, neral, decanal, tolylaldehyde, 2-dodenal, aldehyde C-8, aldehyde C-9, aldehyde C-12, and 2,6-dimethyloctanal. In addition, these flavoring agents may be blended alone or in combination of two or more thereof.

By adding a colorant to the first film layer, the tablet can be colored to improve a palatability and a distinguishability of a coated solid preparation. The colorant improves the palatability and the distinguishability of the tablet, and is not particularly limited as long as it is acceptable for uses such as pharmaceuticals and foods. Examples of the colorant include natural pigments and synthetic pigments.

Specifically, examples of the colorant include cochineal, carmine, curcumin, riboflavin, annatto, titanium oxide, yellow ferric oxide, ferric oxide, talc, pyrogenic silica, magnesium carbonate, and food synthetic colorants such as Food Blue No. 1, Food Blue No. 2, Food Yellow No. 4, Food Yellow No. 5, Food Green No. 3, Food Red No. 2, Food Red No. 3, Food Red No. 102, Food Red No. 104, Food Red No. 105 and Food Red No. 106. In addition, these colorants may be blended alone or in combination of two or more thereof.

By adding a photoprotective agent to the first film layer, the ingredients contained in the tablet can be protected from light. The photoprotective agent imparts a light-shielding property to the tablet, and is not particularly limited as long as it is acceptable for uses such as pharmaceuticals and foods. Examples of the photoprotective agent include oxides and tar dyes.

Specifically, examples of the photoprotective agent include titanium oxide, yellow ferric oxide, ferric oxide, Food Yellow No. 5, and Food Yellow No. 4. In addition, these photoprotective agents may be blended alone or in combination of two or more thereof.

(Film-Coating Method)

Next, a method for coating an uncoated tablet will be described. As a method for film-coating an uncoated tablet, a normal film coated tablet manufacturing method used in this technical field can be used.

Examples of the method for film-coating an uncoated tablet include a film-coating method by a film-coating machine. As a specific example, an uncoated tablet containing an active ingredient and an additive can be coated by charging the uncoated tablet into a film-coating machine, spraying a coating liquid onto the uncoated tablet, and drying the uncoated tablet. The coating liquid is prepared by dissolving and dispersing components contained in the first film layer in an organic solvent such as water, ethanol, hexane, ethyl acetate, and isopropyl alcohol, or a solvent of a mixed solution thereof.

With the above configuration, the first film layer containing the inorganic salt can exert the effect of shortening the disintegration time of the tablet.

Second Film Layer

A purpose of the second film layer is to impart a slipperiness to the tablet. Components of the second film layer are not particularly limited as long as they can be used in fields such as pharmaceuticals and foods. Examples of the components of the second film layer include methacrylic acid-based polymer compounds, water-insoluble substances, and water-soluble substances such as polysaccharides, water-soluble acrylic acid polymers, and cellulose derivatives.

First, the components of the second film layer will be described in detail.

(Thickener)

The thickener has a solubility in water and a viscosity and imparts a slipperiness to the surface of the tablet, and is not particularly limited as long as it is acceptable for uses such as pharmaceuticals and foods. Examples of the thickener include polysaccharides, water-soluble acrylic acid polymers, and cellulose derivatives, preferably include sodium alginate, xanthan gum, guar gum, carrageenan, gellan gum, pectin, gum arabic, locust bean gum, carboxyvinyl polymers, hydroxypropyl methylcellulose, and hydroxypropylcellulose, and more preferably include sodium alginate and xanthan gum. In addition, these thickeners may be blended alone or in combination of two or more thereof.

The inorganic salt contained in the first film layer is preferably at least one selected from the group consisting of potassium phosphate, sodium hydrogen carbonate and potassium chloride, and the thickener contained in the second film layer is preferably at least one selected from the group consisting of alginic acid and xanthan gum. The tablet swallowability and the effect of preventing delay in disintegration time of the uncoated tablet can be further improved by limiting the inorganic salt contained in the first film layer and the thickener contained in the second film layer to respective specific compounds.

Preferred combinations of the inorganic salt contained in the first film layer and the thickener contained in the second film layer include the following (a) and (b).

(a) The inorganic salt contained in the first film layer is at least one selected from the group consisting of potassium phosphate, sodium hydrogen carbonate and potassium chloride, and the thickener contained in the second film layer is alginic acid.

(b) The inorganic salt contained in the first film layer is at least one selected from the group consisting of potassium phosphate, sodium hydrogen carbonate and potassium chloride, and the thickener contained in the second film layer is xanthan gum.

Specific examples of the viscosity of the thickener include sodium alginate having a 1% by mass aqueous solution viscosity at 20° C. of 500 mPa·s or more, xanthan gum having a 1% by mass aqueous solution viscosity at 20° C. of 1000 mPa·s or more, guar gum having a 1% by mass aqueous solution viscosity at 20° C. of 1000 mPa·s or more, carrageenan having a 1% by mass aqueous solution viscosity at 25° C. of 100 mPa·s or more, locust bean gum having a 1% by mass aqueous solution viscosity at 25° C. of 1000 mPa·s or more, a carboxyvinyl polymer having a 2% by mass aqueous solution viscosity at 20° C. of 100 mPa·s or more, hydroxypropyl methylcellulose having a 2% by mass aqueous solution viscosity at 20° C. of 150 mPa·s or more, and hydroxypropylcellulose having a 2% by mass aqueous solution viscosity at 20° C. of 1000 mPa·s or more.

Preferred thickeners are sodium alginate and xanthan gum from the viewpoint of improving the slipperiness of the surface of the tablet in a case of being in contact with water and facilitating swallowing of the tablet. In addition, these thickeners may be blended alone or in combination of two or more thereof.

It should be noted that the viscosity of the thickener can be measured by the capillary viscometer method or the like prescribed in the 17th revised Japanese Pharmacopoeia.

A content of the thickener in the second film layer is not particularly limited, and is preferably, for example, 10% by mass or more and 50% by mass or less with respect to the mass of the second film layer. A lower limit value thereof is more preferably 13% by mass or more, still more preferably 15% by mass or more, and particularly preferably 20% by mass or more. On the other hand, an upper limit value thereof is more preferably 47% by mass or less, still more preferably 45% by mass or less, and particularly preferably 40% by mass or less. The tablet swallowability can be improved by setting the content of the thickener in the second film layer within the range.

As one aspect of the present invention, a film coated tablet is preferred in which the content of the inorganic salt in the first film layer is 20 to 55% by mass, and the content of the thickener in the second film layer is 20 to 40% by mass. The tablet swallowability and the effect of preventing delay in disintegration time of the uncoated tablet can be further improved by controlling the content of the inorganic salt contained in the first film layer and the content of the thickener contained in the second film layer.

As one aspect of the present invention, a mass ratio of the inorganic salt contained in the first film layer to the thickener contained in the second film layer is preferably 1:1 to 4:1, more preferably 3:1, and still more preferably 4:1. The tablet swallowability and the effect of preventing delay in disintegration time of the uncoated tablet can be further improved by controlling the mass ratio of the content of the inorganic salt contained in the first film layer to the content of the thickener contained in the second film layer.

(Water-Soluble Film Base of Second Film Layer)

The water-soluble film base is a base in a composition for coating an uncoated tablet, and is not particularly limited as long as it is acceptable for uses such as pharmaceuticals and foods. Examples of the water-soluble film base include cellulose derivatives, synthetic resins and polysaccharides.

In addition, a viscosity of the water-soluble film base is not particularly limited, but a low-viscosity polymer that rapidly dissolves in water is preferred. Regarding the viscosity of the water-soluble film base, for example, the 2% by mass aqueous solution viscosity at 20° C. thereof is preferably 0.1 mPa·s or more and 50 mPa·s or less. A lower limit value thereof is more preferably 1 mPa·s or more, still more preferably 2 mPa·s or more, and particularly preferably 3 mPa·s or more. On the other hand, an upper limit value thereof is more preferably 45 mPa·s or less, still more preferably 40 mPa·s or less, and particularly preferably 35 mPa·s or less. It should be noted that the viscosity of the water-soluble film base can be measured by the capillary viscometer method or the like prescribed in the 17th revised Japanese Pharmacopoeia.

Specifically, examples of the water-soluble film base include hydroxypropyl methylcellulose (2% by mass aqueous solution viscosity at 20° C. is 15 mPa·s or less), hydroxypropylcellulose (2% by mass aqueous solution viscosity at 20° C. is 10 mPa·s or less), polyvinyl alcohol (4% by mass aqueous solution viscosity at 20° C. is 6 mPa·s or less), polyvinylpyrrolidone (average molecular weight of 40,000 or less), methylcellulose (2% by mass aqueous solution viscosity at 20° C. is 15 mPa·s or less), and pullulan (10% by mass aqueous solution viscosity at 30° C. is 15 to 180 mPa·s). Preferred water-soluble film bases are hydroxypropyl methylcellulose and hydroxypropylcellulose from the viewpoint of being excellent in easy availability and ease of coating. In addition, these water-soluble film bases may be blended alone or in combination of two or more thereof.

A content of the water-soluble film base in the second film layer is not particularly limited, and is preferably, for example, 30% by mass or more and 70% by mass or less with respect to the mass of the second film layer. A lower limit value thereof is more preferably 33% by mass or more, still more preferably 35% by mass or more, and particularly preferably 40% by mass or more. On the other hand, an upper limit value thereof is more preferably 67% by mass or less, still more preferably 65% by mass or less, and particularly preferably 60% by mass or less. A tablet having an excellent coating property can be obtained by setting the content of the water-soluble film base in the second film layer within the range.

(Other Components)

In addition to the thickener and the water-soluble film base, the second film layer may contain other components as necessary. Similar to the first film layer, specific examples of components to be added include plasticizers, sweeteners, flavoring agents, colorants, and photoprotective agents.

It should be noted that in order to maintain a function of the second film layer of imparting the slipperiness to the surface of the tablet and improving the swallowability, and to effectively exhibit the function of the first film layer in the gastrointestinal tract, it is preferred that inorganic salts such as potassium phosphate, sodium hydrogen carbonate, and sodium chloride that dissolve in water and react with the thickener are not blended in the second film layer.

(Film-Coating Method)

Next, a method for coating an uncoated tablet having the first film layer with the second film layer will be described.

As a method for film-coating an uncoated tablet having the first film layer, a normal film coated tablet manufacturing method used in this technical field can be used. As the method for film-coating an uncoated tablet having the first film layer, for example, an uncoated tablet having the first film layer can be coated by charging the uncoated tablet into a film-coating machine, spraying a coating liquid onto the uncoated tablet, and drying the uncoated tablet. The coating liquid is prepared by dissolving and dispersing components contained in the second film layer in an organic solvent such as water, ethanol, hexane, ethyl acetate, and isopropyl alcohol, or a solvent of a mixed solution thereof.

With the above configuration, the second film layer containing the thickener can exert the effect of imparting the slipperiness to the surface of the tablet and improving the tablet swallowability.

Uncoated Tablet

The uncoated tablet contains an active ingredient, and a formulation of the uncoated tablet is not particularly limited and does not affect the film layers. First, components of the uncoated tablet will be described in detail (Active Ingredient)

The active ingredient exerts an efficacy and effect, and is not particularly limited as long as it is acceptable for uses such as pharmaceuticals and foods. Examples of the active ingredient include pharmaceutical ingredients and functional ingredients used in pharmaceuticals, quasi-drugs, OTC drugs, herbal medicines, crude drugs, cosmetics, cosmetic materials, health foods, supplements, etc.

Specifically, examples of the pharmaceutical ingredients and the functional ingredients include lipid regulating agents, antidiabetic agents, appetite suppressants, antihypertensive agents, vasodilators, beta-adrenergic receptor blockers, cardiotonic ion channel agents, antiarrhythmics, anticoagulants, hemostatic agents, anti-inflammatory agents, analgesics, antiallergic agents, immunosuppressant drugs, corticosteroids, steroids, antitumor agents, central nerve function improvers, sympathomimetic agents, parasympathomimetic agents, antimuscarinic agents, dopaminergic agents, antidiarrheal agents, antiemetic agents, sedatives, astringents, tranquilizers, antidepressants, antiepileptics, anxiolytics, hypnotic agents, stimulants, bronchodilators, antitussive agents, diuretics, muscle relaxants, bisphosphonates, antibiotics, antiviral agents, diagnostic agents, diagnostic imaging agents, radiopharmaceuticals, animal-derived substances, plant-derived substances, lapidine, nobiletin, sulforaphane, ampelopsin, curcumins, resveratrols, geraniol, osajin, isoliquiritigenin, hydroxytyrosol, 25-hydroxycholecalciferol, coenzyme Q-10, S-adenosylmethionine, anthocyanin, ascorbic acid 2-glucoside, proteoglycan, N-acetylglucosamine, collagen, bilberry extract, carrot powders, gokahi, licorice, peony, cinnamon bark, fennel, amomum seeds, bifidobacteria, lactic acid bacteria, yeast, vitamins such as vitamin A, vitamin B, and vitamin C, minerals such as calcium, magnesium, and iron, dietary fibers such as polydextrose, fatty acids, polyphenols, proteins, amino acids, oligosaccharides, lecithin, carotenoids, and chlorophyll. In addition, these pharmaceutical ingredients and functional ingredients may be blended alone or in combination of two or more thereof.

(Other Components)

In addition to the active ingredient, the uncoated tablet may contain an additive as necessary. Specifically, examples of the additive include excipients, binders, disintegrants, lubricants, stabilizers, preservatives, and colorants.

By adding an excipient to the uncoated tablet, a bulk of the uncoated tablet can be adjusted to make it easier to take the tablet. The excipient adjusts the bulk of the uncoated tablet, and is not particularly limited as long as it is acceptable for uses such as pharmaceuticals and foods. Examples of the excipient include sugars, phosphates, and sulfates.

Specifically, examples of the excipient include crystalline cellulose, lactose, sucrose, mannitol, glucose, starch, and calcium phosphate. In addition, these excipients may be blended alone or in combination of two or more thereof.

By adding a binder to the uncoated tablet, a binding force is imparted to a powder component, and a stable solid preparation can be manufactured. The binder enhances the binding force of the powder component and imparts a tablet hardness, and is not particularly limited as long as it is acceptable for uses such as pharmaceuticals and foods. Examples of the binder include cellulose derivatives, synthetic resins, sugars, polyethers, and waxes.

Specifically, examples of the binder include carboxymethylcellulose, hydroxyethylcellulose, hydroxypropyl methylcellulose, hydroxypropylcellulose, polyvinylpyrrolidone, polyvinyl alcohol, polyacrylic acids, polymethacrylic acids, glucose, sucrose, lactose, maltose, dextrin, sorbitol, mannitol, polyethylene glycol, paraffin, gum arabic, gelatin, agar, starch, and pullulan. In addition, these binders may be blended alone or in combination of two or more thereof.

By adding a disintegrant, tablet disintegration can be accelerated and absorption can be improved. The disintegrant enhances water absorption to disintegrate the tablet, and is not particularly limited as long as it is acceptable for uses such as pharmaceuticals and foods. Examples of the disintegrant include sugars, cellulose derivatives, synthetic resins, and alginates.

Specifically, examples of the disintegrant include corn starch, low-substituted hydroxypropylcellulose, carboxymethylcellulose calcium, crystalline cellulose, croscarmellose sodium, sodium carboxymethyl starch, crospovidone, and sodium starch glycolate. In addition, these disintegrants may be blended alone or in combination of two or more thereof.

By adding a lubricant, it is possible to prevent occurrence of tableting problems such as sticking during manufacture of the tablet. The lubricant reduces an adhesive force of a powder component and increases a fluidity thereof, and is not particularly limited as long as it is acceptable for uses such as pharmaceuticals and foods. Examples of the lubricant include phyllosilicate mineral powders, silicon oxides, saturated fatty acids, esters, waxes, hydrogenated vegetable oils, fats, and polyethers.

Specifically, examples of the lubricant include talc, light anhydrous silicic acids, magnesium stearate, calcium stearate, magnesium carbonate, sodium benzoate, palmitic acids, sodium stearyl fumarate, sucrose fatty acid ester, beeswaxes, soybean hardened oils, cacao butter, and polyethylene glycol. In addition, these lubricants may be blended alone or in combination of two or more thereof.

By adding a stabilizer, deactivation of the active ingredient can be prevented. The stabilizer prevents chemical decomposition and physical decomposition of the active ingredient, and is not particularly limited as long as it is acceptable for uses such as pharmaceuticals and foods. Examples of the stabilizer include inorganic compounds, organic acids, organic acid salts, and vitamins.

Specifically, examples of the stabilizer include sodium bisulfite, ascorbic acids, sodium edetate, and tocopherol. In addition, these stabilizers may be blended alone or in combination of two or more thereof.

By adding a preservative, contamination of the tablet by microorganisms can be prevented. The preservative inhibits growth of microorganisms, and is not particularly limited as long as it is acceptable for uses such as pharmaceuticals and foods. Examples of the preservative include benzoate salts and paraoxybenzoic acid esters.

Specifically, examples of the preservative include sodium benzoate, propyl parahydroxybenzoate, methylparaben, and propylparaben. In addition, these preservatives may be blended alone or in combination of two or more thereof.

By adding a colorant, the tablet can be colored to improve a palatability and a distinguishability of a coated solid preparation. The colorant improves the palatability and the distinguishability of the tablet, and is not particularly limited as long as it is acceptable for uses such as pharmaceuticals and foods. Examples of the colorant include natural pigments and synthetic pigments.

Specifically, examples of the colorant include cochineal, carmine, curcumin, riboflavin, annatto, titanium oxide, yellow ferric oxide, ferric oxide, talc, pyrogenic silica, magnesium carbonate, and food synthetic colorants such as Food Blue No. 1, Food Blue No. 2, Food Yellow No. 4, Food Yellow No. 5, Food Green No. 3, Food Red No. 2, Food Red No. 3, Food Red No. 102, Food Red No. 104, Food Red No. 105 and Food Red No. 106. In addition, these colorants may be blended alone or in combination of two or more thereof.

Examples of other additives include dissolution aids, surfactants, emulsifiers, antioxidants, brighteners, foaming agents, desiccants, antiseptic agents, fluidizers, sweeteners, taste masking agents, cooling agents, flavors, perfumes, fragrances, and disintegration aids. In addition, these additives may be blended alone or in combination of two or more thereof.

Next, a method for manufacturing the uncoated tablet will be described. As the method for manufacturing the uncoated tablet, a normal method used in this technical field can be used. As a process for manufacturing the uncoated tablet, the mixed active ingredient and additive may be directly compressed into tablets, or the active ingredient and the additive may be granulated and then compressed into tablets.

A granulation method is not particularly limited. Examples thereof include a dry granulation method and a wet granulation method, and more specific examples thereof include a fluidized bed granulation method, a tumbling granulation method, a stirring granulation method, and a spray granulation method.

A mixer used in a mixing process is not particularly limited, and examples thereof include tumbler mixers, V-type mixers, double cone mixers, and infinite mixers. A tableting machine used in a tableting process is not particularly limited, and examples thereof include a single-punch tableting machine and a rotary tableting machine.

With the above configuration, the uncoated tablet can contain various active ingredients, and thus a film coated tablet having a broad range of efficacy and effect can be provided.

Applications of Film Coated Tablet

The applications of the film coated tablet will be described in detail. The applications of the film coated tablet are not particularly limited, and examples thereof include pharmaceuticals, quasi-drugs, cosmetic materials for drinking, cosmetics for drinking, health foods (nutritional supplements, foods with nutrient function claims, foods for the sick, food for specified health use, foods with functional claims, etc.), and supplements.

With the above configuration, the film coated tablet can exhibit a high versatility.

EXAMPLES

Examples of the present invention will be described below, but the present invention is not limited to these examples, and various modifications are possible within the technical concept of the present invention.

(Preparation of Test Sample)

Test Example 1

The uncoated tablet was prepared as follows without performing a granulation process. A mixture was obtained by mixing 6480 g of lactose (Tablettose 80, Meggle Japan Co. Ltd.), 1040 g of crystalline cellulose (Ceolus PH101, Asahi Kasei Co., Ltd.), 400 g of hydroxypropylcellulose (HPC-L, Nippon Soda Co., Ltd.), and 80 g of magnesium stearate (Partek, Merck Co., Ltd.) with a mixer (Type TBM-25, Tokuju Corporation).

The uncoated tablet was prepared with a diameter of 8 mm, a thickness of 4.9 mm and a weight of 260 mg by compressing the mixture into tablets by a rotary tableting machine (Type HT-AP15, Hata Iron Works Co., Ltd.) under a condition of a tableting pressure of 880 kg.

The film coated tablet was prepared as in Examples 1 to 11 below.

Example 1

A first coating liquid was obtained by adding, dissolving and dispersing 0.84 parts by mass of a glycerin fatty acid ester (Myvacet 9-45K, Koyo Shokai Co., Ltd.), 6.66 parts by mass of sodium chloride (special grade, Fujifilm Wako Pure Chemical Co., Ltd.), and 5.00 parts by mass of hydroxypropylcellulose (HPC-SSL, Nippon Soda Co., Ltd.) to and in a mixed liquid containing 39.83 parts by mass of anhydrous ethanol and 48.13 parts by mass of purified water.

A second coating liquid was obtained by adding, dissolving and dispersing 1.00 part by mass of a glycerin fatty acid ester, 1.50 parts by mass of sorbitol (Sorbitol FP, B Food Science Co., Ltd.), 0.38 parts by mass of acesulfame potassium (Sunett D, MC Food Specialties Co., Ltd.), 6.00 parts by mass of hydroxypropylcellulose (HPC-SSL, Nippon Soda Co., Ltd.), 0.12 parts by mass of talc (Crown Talc Pharmacopoeia PP, Kihara Kasei Co., Ltd.), and 6.00 parts by mass of sodium alginate (Kimica Algin I-8-270, Kimica Co., Ltd.) to and in a mixed liquid containing 75.40 parts by mass of anhydrous ethanol and 9.60 parts by mass of purified water.

150 g of the uncoated tablets obtained in Test Example 1 were charged into a drum-type tablet coating machine (Type DRC-200, Powrex Co., Ltd.), and coated by being sprayed with the first coating liquid in an amount of 2 parts by mass of the first coating liquid per 100 parts by mass of the uncoated tablet in terms of solid content mass. Then, the uncoated tablets were coated by being sprayed with the second coating liquid in an amount of 2 parts by mass of the second coating liquid per 100 parts by mass of the uncoated tablet in terms of solid content mass.

Example 2

Similar to Example 1, the uncoated tablets in Test Example 1 were coated with the first coating liquid in an amount of 4 parts by mass of the first coating liquid per 100 parts by mass of the uncoated tablet in Test Example 1 in terms of solid content mass. Then, the uncoated tablets were coated with the second coating liquid in an amount of 2 parts by mass of the second coating liquid per 100 parts by mass of the uncoated tablet in terms of solid content mass.

Example 3

Similar to Example 1, the uncoated tablets in Test Example 1 were coated with the first coating liquid in an amount of 6 parts by mass of the first coating liquid per 100 parts by mass of the uncoated tablet in Test Example 1 in terms of solid content mass, and then coated with the second coating liquid in an amount of 2 parts by mass of the second coating liquid per 100 parts by mass of the uncoated tablet in terms of solid content mass.

Example 4

A first coating liquid was obtained by adding, dissolving and dispersing 0.84 parts by mass of a glycerin fatty acid ester (Myvacet 9-45K, Koyo Shokai Co., Ltd.), 2.50 parts by mass of sodium hydrogen carbonate (special grade, Fujifilm Wako Pure Chemical Co., Ltd.), and 9.16 parts by mass of hydroxypropylcellulose (HPC-SSL, Nippon Soda Co., Ltd.) to and in a mixed liquid containing 39.83 parts by mass of anhydrous ethanol and 48.13 parts by mass of purified water.

A second coating liquid was obtained by adding, dissolving and dispersing 1.00 part by mass of a glycerin fatty acid ester, 1.50 parts by mass of sorbitol (Sorbitol FP, B Food Science Co., Ltd.), 0.38 parts by mass of acesulfame potassium (Sunett D, MC Food Specialties Co., Ltd.), 6.00 parts by mass of hydroxypropylcellulose (HPC-SSL, Nippon Soda Co., Ltd.), 0.12 parts by mass of talc (Crown Talc Pharmacopoeia PP, Kihara Kasei Co, Ltd.), and 6.00 parts by mass of sodium alginate (Kimica Algin I-8-270, Kimica Co., Ltd.) to and in a mixed liquid containing 75.40 parts by mass of anhydrous ethanol and 9.60 parts by mass of purified water.

150 g of the uncoated tablets obtained in Test Example 1 were charged into a drum-type tablet coating machine (Type DRC-200, Powrex Co., Ltd.), and coated by being sprayed with the first coating liquid in an amount of 2 parts by mass of the first coating liquid per 100 parts by mass of the uncoated tablet in terms of solid content mass. Then, the uncoated tablets were coated by being sprayed with the second coating liquid in an amount of 2 parts by mass of the second coating liquid per 100 parts by mass of the uncoated tablet in terms of solid content mass.

Example 5

A first coating liquid was obtained by adding, dissolving and dispersing 0.84 parts by mass of polyethylene glycol 6000 (Macrogol 6000R, NOF Corporation), 6.66 parts by mass of sodium hydrogen carbonate (special grade, Fujifilm Wako Pure Chemical Co., Ltd.), and 5.00 parts by mass of hydroxypropylcellulose (HPC-SSL, Nippon Soda Co., Ltd.)

to and in 87.51 parts by mass of purified water. A second coating liquid was prepared in the same manner as in Example 4.

150 g of the uncoated tablets obtained in Test Example 1 were charged into a drum-type tablet coating machine (Type DRC-200, Powrex Co., Ltd.), and coated by being sprayed with the first coating liquid in an amount of 2 parts by mass of the first coating liquid per 100 parts by mass of the uncoated tablet in terms of solid content mass. Then, the uncoated tablets were coated by being sprayed with the second coating liquid in an amount of 2 parts by mass of the second coating liquid per 100 parts by mass of the uncoated tablet in terms of solid content mass.

Example 6

A first coating liquid was obtained by adding, dissolving and dispersing 0.84 parts by mass of a glycerin fatty acid ester (Myvacet 9-45K, Koyo Shokai Co., Ltd.), 6.66 parts by mass of potassium dihydrogen phosphate (special grade, Fujifilm Wako Pure Chemical Co., Ltd.), and 5.00 parts by mass of hydroxypropylcellulose (HPC-SSL, Nippon Soda Co., Ltd.) to and in a mixed liquid containing 39.83 parts by mass of anhydrous ethanol and 48.13 parts by mass of purified water.

A second coating liquid was obtained by adding, dissolving and dispersing 1.00 part by mass of a glycerin fatty acid ester, 1.50 parts by mass of sorbitol (Sorbitol FP, B Food Science Co., Ltd.), 0.38 parts by mass of acesulfame potassium (Sunett D, MC Food Specialties Co., Ltd.), 6.00 parts by mass of hydroxypropylcellulose (HPC-SSL, Nippon Soda Co., Ltd.), 0.12 parts by mass of talc (Crown Talc Pharmacopoeia PP, Kihara Kasei Co., Ltd.), and 6.00 parts by mass of sodium alginate (Kimica Algin I-8-270, Kimica Co., Ltd.) to and in a mixed liquid containing 75.40 parts by mass of anhydrous ethanol and 9.60 parts by mass of purified water.

150 g of the uncoated tablets obtained in Test Example 1 were charged into a drum-type tablet coating machine (Type DRC-200, Powrex Co., Ltd.), and coated by being sprayed with the first coating liquid in an amount of 4 parts by mass of the first coating liquid per 100 parts by mass of the uncoated tablet in terms of solid content mass. Then, the uncoated tablets were coated by being sprayed with the second coating liquid in an amount of 2 parts by mass of the second coating liquid per 100 parts by mass of the uncoated tablet in terms of solid content mass.

Example 7

Similar to Example 5, the uncoated tablets in Test Example 1 were coated by being sprayed with the first coating liquid in an amount of 4 parts by mass of the first coating liquid per 100 parts by mass of the uncoated tablet in Test Example 1 in terms of solid content mass. Then, the uncoated tablets in Test Example 1 were coated by being sprayed with the second coating liquid in an amount of 4 parts by mass of the second coating liquid per 100 parts by mass of the uncoated tablet in Test Example 1 in terms of solid content mass.

Example 8

A first coating liquid was obtained by adding, dissolving and dispersing 0.84 parts by mass of polyethylene glycol 6000 (Macrogol 6000R, NOF Corporation), 6.66 parts by mass of sodium hydrogen carbonate (special grade, Fujifilm Wako Pure Chemical Co., Ltd.), and 5.00 parts by mass of hydroxypropylcellulose (HPC-SSL, Nippon Soda Co., Ltd.) to and in 87.51 parts by mass of purified water.

A second coating liquid was obtained by adding, dissolving and dispersing 1.00 part by mass of a glycerin fatty acid ester, 1.50 parts by mass of sorbitol (Sorbitol FP, B Food Science Co., Ltd.), 0.38 parts by mass of acesulfame potassium (Sunett D, MC Food Specialties Co., Ltd.), 9.00 parts by mass of hydroxypropylcellulose (HPC-SSL, Nippon Soda Co., Ltd.), 0.12 parts by mass of talc (Crown Talc Pharmacopoeia PP, Kihara Kasei Co., Ltd.), and 3.00 parts by mass of sodium alginate (Kimica Algin I-8-270, Kimica Co., Ltd.) to and in a mixed liquid containing 75.40 parts by mass of anhydrous ethanol and 9.60 parts by mass of purified water.

150 g of the uncoated tablets obtained in Test Example 1 were charged into a drum-type tablet coating machine (Type DRC-200, Powrex Co., Ltd.), and coated by being sprayed with the first coating liquid in an amount of 2 parts by mass of the first coating liquid per 100 parts by mass of the uncoated tablet in terms of solid content mass. Then, the uncoated tablets were coated by being sprayed with the second coating liquid in an amount of 2 parts by mass of the second coating liquid per 100 parts by mass of the uncoated tablet in terms of solid content mass.

Example 9

The first coating liquid in Example 5 was prepared. A second coating liquid was obtained by adding, dissolving and dispersing 1.00 part by mass of a glycerin fatty acid ester, 1.50 parts by mass of sorbitol (Sorbitol FP, B Food Science Co., Ltd.), 0.38 parts by mass of acesulfame potassium (Sunett D, MC Food Specialties Co., Ltd.), 6.00 parts by mass of hydroxypropylcellulose (HPC-SSL, Nippon Soda Co., Ltd.), 0.12 parts by mass of talc (Crown Talc Pharmacopoeia PP, Kihara Kasei Co., Ltd.), and 6.00 parts by mass of xanthan gum (Grinsted Xanthan 200, Danisco Japan Co., Ltd.) to and in a mixed liquid containing 75.40 parts by mass of anhydrous ethanol and 9.60 parts by mass of purified water.

150 g of the uncoated tablets obtained in Test Example 1 were charged into a drum-type tablet coating machine (Type DRC-200, Powrex Co., Ltd.), and coated by being sprayed with the first coating liquid in an amount of 2 parts by mass of the first coating liquid per 100 parts by mass of the uncoated tablet in terms of solid content mass. Then, the uncoated tablets were coated by being sprayed with the second coating liquid in an amount of 2 parts by mass of the second coating liquid per 100 parts by mass of the uncoated tablet in terms of solid content mass.

Comparative Example 1

A coating liquid was obtained by adding, dissolving and dispersing 0.84 parts by mass of a glycerin fatty acid ester, 11.66 parts by mass of hydroxypropylcellulose (HPC-SSL, Nippon Soda Co., Ltd.) to and in a mixed liquid containing 39.83 parts by mass of anhydrous ethanol and 48.13 parts by mass of purified water.

150 g of the uncoated tablets obtained in Test Example 1 were charged into a drum-type tablet coating machine (Type DRC-200, Powrex Co., Ltd.), and coated by being sprayed with the coating liquid in an amount of 2 parts by mass of the coating liquid per 100 parts by mass of the uncoated tablet in terms of solid content mass.

Comparative Example 2

A coating liquid was obtained by adding, dissolving and dispersing 1.00 part by mass of a glycerin fatty acid ester, 1.50 parts by mass of sorbitol, 0.38 parts by mass of acesulfame potassium, 6.00 parts by mass of hydroxypropylcellulose (HPC-SSL, Nippon Soda Co., Ltd.), 0.12 parts by mass of talc, and 6.00 parts by mass of sodium alginate to and in a mixed liquid containing 75.40 parts by mass of anhydrous ethanol and 9.60 parts by mass of purified water.

150 g of the uncoated tablets obtained in Test Example 1 were charged into a drum-type tablet coating machine (Type DRC-200, Powrex Co., Ltd.), and coated by being sprayed with the coating liquid in an amount of 2 parts by mass of the coating liquid per 100 parts by mass of the uncoated tablet in terms of solid content mass.

Comparative Example 3

A first coating liquid was obtained by adding, dissolving and dispersing 0.84 parts by mass of a glycerin fatty acid ester, 11.66 parts by mass of hydroxypropylcellulose (HPC-SSL, Nippon Soda Co., Ltd.) to and in a mixed liquid containing 39.83 parts by mass of anhydrous ethanol and 48.13 parts by mass of purified water. A second coating liquid was obtained by adding, dissolving and dispersing 1.00 part by mass of a glycerin fatty acid ester, 1.50 parts by mass of sorbitol, 0.38 parts by mass of acesulfame potassium, 6.00 parts by mass of hydroxypropylcellulose (HPC-SSL, Nippon Soda Co., Ltd.), 0.12 parts by mass of talc, and 6.00 parts by mass of sodium alginate to and in a mixed liquid containing 75.40 parts by mass of anhydrous ethanol and 9.60 parts by mass of purified water.

150 g of the uncoated tablets obtained in Test Example 1 were charged into a drum-type tablet coating machine (Type DRC-200, Powrex Co., Ltd.), and coated by being sprayed with the first coating liquid in an amount of 4 parts by mass of the first coating liquid per 100 parts by mass of the uncoated tablet in terms of solid content mass. Then, the uncoated tablets were coated by being sprayed with the second coating liquid in an amount of 2 parts by mass of the second coating liquid per 100 parts by mass of the uncoated tablet in terms of solid content mass.

(Disintegration Test)

The disintegration test was performed on a test sample according to a disintegration test method prescribed in the 17th revised Japanese Pharmacopoeia (water, $37 \pm 2^\circ$ C., with an auxiliary plate).

Regarding a disintegration ability of a tablet, it is preferred that a difference with a disintegration time of an uncoated tablet is small, for example, within 20 minutes, and more preferably within 10 minutes.

(Tablet Slipperiness Test)

Figure 2:
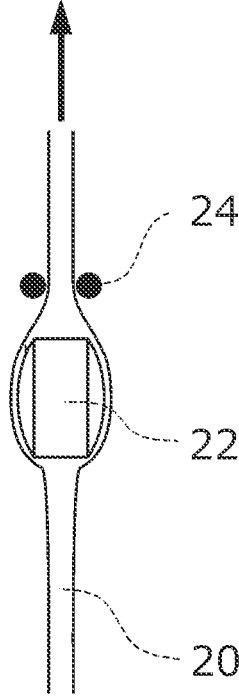
FIG. 2 is a schematic diagram illustrating a method for a tablet slipperiness test.

FIG. 2 shows a schematic diagram illustrating a method for the tablet slipperiness test. As shown in FIG. 2, the tablet slipperiness test is conducted by putting a tablet 22 in a silicone tube 20 and fixing the tablet 22, then adding 50 μL of water and leaving for 2 minutes, and thereafter, measuring, by using a small desktop testing machine (EZ-SX type 50N, manufactured by Shimadzu Corporation), a pull-up stress in a direction indicated by an arrow of the silicone tube 20 (SKSQ-0828, Fuso Rubber Industry Co., Ltd.) from between fixing pins 24 installed at intervals of 4 mm.

The tablet preferably has a slipperiness such that the pull-up stress thereof is as lower as possible as compared with a tablet having a similar shape to which the slipperiness is not imparted.

Results

Next, Tables 1 to 4 show the results of the disintegration test and tablet slipperiness test for each test example, each example, and each comparative example. It should be noted that a unit of each component amount in the tables is mg. In addition, each value is rounded off to two decimal places and expressed in the second decimal place.

TABLE 1

| | Items | Test Example 1 | Comparative Example 1 | Comparative Example 2 | Comparative Example 3 |
|---|---|---|---|---|---|
| | Uncoated tablet | 260.00 | 260.00 | 260.00 | 260.00 |
| First film layer | Hydroxypropylcellulose (*1) | 0.00 | 4.85 | 0.00 | 9.70 |
| | Others | 0.00 | 0.35 | 0.00 | 0.70 |
| | Subtotal | 0.00 | 5.20 | 0.00 | 10.40 |
| Second film layer (*2) | Sodium alginate | 0.00 | 0.00 | 2.08 | 2.08 |
| | Hydroxypropylcellulose (*1) | 0.00 | 0.00 | 2.08 | 2.08 |
| | Others | 0.00 | 0.00 | 1.04 | 1.04 |
| | Subtotal | 0.00 | 0.00 | 5.20 | 5.20 |
| Evaluation indexes | Disintegration time (min) | 7 | 6 | 50 | 29 |
| | Disintegration time difference with uncoated tablet (min) | — | −1 | +43 | +22 |
| | Tablet slipperiness (gf) | Not measured | 557 | 230 | 192 |

*1 hydroxypropylcellulose (2% by mass aqueous solution viscosity at 20° C. is 10 mPa·s or less)

*2 treated as the first film layer in Comparative Example 2.

Table 1 shows results of test samples containing no inorganic salt in the first film layer. As shown in Table 1, when Comparative Examples 1 and 3 are compared, it was found that the slipperiness of the tablet is improved by blending sodium alginate in the film layer, which is the outer layer. In addition, in a case in which Comparative Examples 2 and 3 are compared, when a film layer containing sodium alginate is provided, in Comparative Example 2 in which the film layer, which is the inner layer, is not provided and Comparative Example 3 in which the first film layer does not contain an inorganic salt, a clear delay in disintegration time was observed as compared with the disintegration time of the uncoated tablet (Test Example 1).

Table 2 shows results of test samples containing an inorganic salt in the first film layer and a thickener in the second film layer. As shown in Table 2, when Examples 1 to 5 and Comparative Examples 1 to 3 in Table 1 are compared, in a film coated tablet containing sodium alginate as a thickener in the second film layer, by blending sodium chloride and sodium hydrogen carbonate as inorganic salts in the first film layer, the delay in disintegration time was significantly prevented. In addition, it was found that the slipperiness of each film coated tablet in Examples 1-5 is significantly improved.

TABLE 2

| | Items | Example 1 | Example 2 | Example 2 | Example 4 | Example 5 |
|---|---|---|---|---|---|---|
| | Uncoated tablet | 260.00 | 260.00 | 260.00 | 260.00 | 260.00 |
| First film layer | Hydroxypropylcellulose (*1) | 2.08 | 4.16 | 6.24 | 3.81 | 2.08 |
| | Sodium chloride | 2.77 | 5.54 | 8.31 | 0.00 | 0.00 |
| | Sodium hydrogen carbonate | 0.00 | 0.00 | 0.00 | 1.04 | 2.77 |
| | Others | 0.35 | 0.70 | 1.05 | 0.35 | 0.35 |
| | Subtotal | 5.20 | 10.40 | 15.60 | 5.20 | 5.20 |
| Second film layer | Sodium alginate | 2.08 | 2.08 | 2.08 | 2.08 | 2.08 |
| | Hydroxypropylcellulose (*1) | 2.08 | 2.08 | 2.08 | 2.08 | 2.08 |
| | Others | 1.04 | 1.04 | 1.04 | 1.04 | 1.04 |
| | Subtotal | 5.20 | 5.20 | 5.20 | 5.20 | 5.20 |
| Evaluation indexes | Disintegration time (min) | 10 | 9 | 6 | 11 | 5 |
| | Disintegration time difference with uncoated tablet (min) | +3 | +2 | −1 | +4 | −2 |
| | Tablet slipperiness (gf) | 221 | 213 | 204 | — | 208 |

(*1) hydroxypropylcellulose (2% by mass aqueous solution viscosity at 20° C. is 10 mPa · s or less)

TABLE 3

| Items | | Example 6 | Example 7 | Example 8 | Example 9 |
|---|---|---|---|---|---|
| First film layer | Uncoated tablet | 260.00 | 260.00 | 260.00 | 260.00 |
| | Hydroxypropylcellulose (*1) | 4.16 | 4.16 | 2.08 | 2.08 |
| | Potassium phosphate | 5.54 | 0.00 | 0.00 | 0.00 |
| | Sodium hydrogen carbonate | 0.00 | 5.54 | 2.77 | 2.77 |
| | Others | 0.70 | 0.70 | 0.35 | 0.35 |
| | Subtotal | 10.40 | 10.40 | 5.20 | 5.20 |
| Second film layer | Sodium alginate | 2.08 | 4.16 | 1.04 | 0.00 |
| | Xanthan gum | 0.00 | 0.00 | 0,00 | 2.08 |
| | Hydroxypropylcellulose (*1) | 2.08 | 4,16 | 3.12 | 2.08 |
| | Others | 1.04 | 2.08 | 1.04 | 1.04 |
| | Subtotal | 5.20 | 10.40 | 5.20 | 5.20 |
| Evaluation indexes | Disintegration time (min) | 6 | 8 | 5 | 5 |
| | Disintegration time difference with uncoated tablet (min) | −1 | +1 | −2 | −2 |
| | Tablet slipperiness (gf) | 226 | — | 283 | 211 |

*1 hydroxypropylcellulose (2% by mass aqueous solution viscosity at 20° C. is 10 mPa·s or less)

Table 3 shows results of test samples containing an inorganic salt in the first film layer and a thickener in the second film layer. As shown in Table 3, when Examples 6 to 9 and Comparative Examples 1 to 3 in Table 1 are compared, in a film coated tablet containing sodium alginate and xanthan gum as thickeners in the second film layer, by blending potassium phosphate and sodium hydrogen carbonate as inorganic salts in the first film layer, the delay in disintegration time was significantly prevented. In addition, it was found that the slipperiness of each film coated tablet in Examples 6-9 is significantly improved.

In view of the above, it has become apparent that regarding the film coated tablet, by blending an inorganic salt in the first film layer, which is the inner layer, and blending a thickener in the second film layer, which is the outer layer, the delay in disintegration time is significantly prevented, and the slipperiness of the tablet is greatly improved.

Although the present invention has been described in detail with reference to specific embodiments, it will be apparent to those skilled in the art that various modifications and variations can be made without departing from the spirit and scope of the present invention. This application is based on a Japanese patent application (Japanese Patent Application No. 2020-120267) filed on Jul. 13, 2020, the entire contents of which are incorporated herein by reference.

INDUSTRIAL APPLICABILITY

According to the present invention, it is possible to provide a film coated tablet having an improved disintegration time of a tablet that can be used for pharmaceuticals, quasi-drugs, cosmetic materials for drinking, cosmetics for drinking, health foods (nutritional supplements, foods with nutrient function claims, foods for the sick, food for specified health use, foods with functional claims, etc.), and supplements.

The invention claimed is:

1. A film coated tablet, comprising:

a tablet;

a first film layer that coats the tablet and contains (a) a first water-soluble film base selected from hydroxypropyl methylcellulose, hydroxypropylcellulose, and a combination thereof and (b) an inorganic salt selected from the group consisting of potassium phosphate, sodium hydrogen carbonate, sodium chloride, and a combination thereof; and a second film layer that coats the tablet coated with the first film layer and contains (a) a second water-soluble film base selected from hydroxypropyl methylcellulose, hydroxypropylcellulose, and a combination thereof and (b) a thickener selected from the group consisting of sodium alginate, xanthan gum, and a combination thereof.

2. A film coated tablet, comprising:

a tablet;

a first film layer that coats the tablet and contains (a) a first water-soluble film base selected from hydroxypropyl methylcellulose, hydroxypropylcellulose, and a combination thereof and (b) an inorganic salt selected from the group consisting of potassium phosphate, sodium hydrogen carbonate, sodium chloride, and a combination thereof; and a second film layer that coats an outside of the first film layer and contains (a) a second water-soluble film base selected from hydroxypropyl methylcellulose, hydroxypropylcellulose, and a combination thereof and (b) a thickener selected from the group consisting of sodium alginate, xanthan gum, and a combination thereof, wherein the inorganic salt in the first film layer reduces a viscosity of the thickener contained in the second film layer.

3. A film coated tablet, comprising:

a tablet;

a first film layer that coats the tablet and contains (a) a first water-soluble film base selected from hydroxypropyl methylcellulose, hydroxypropylcellulose, and a combination thereof and (b) an inorganic salt selected from the group consisting of potassium phosphate, sodium hydrogen carbonate, sodium chloride, and a combination thereof; and a second film layer that coats an outside of the first film layer and contains (a) a second water-soluble film base selected from hydroxypropyl methylcellulose, hydroxypropylcellulose, and a combination thereof and (b) a thickener selected from the group consisting of sodium alginate, xanthan gum, and a combination thereof, wherein the first water-soluble film base has a 2% by mass aqueous solution viscosity at 20° C. of 100 mPa·s or less.

4. The film-coated tablet according to claim 1, wherein a content of the inorganic salt in the first film layer is 20 to 55% by mass, and a content of the thickener in the second film layer is 20 to 40% by mass.

5. The film-coated tablet according to claim 1, wherein the first film layer is 2 to 6 parts by mass per 100 parts by mass of the tablet, and the second film layer is 2 to 4 parts by mass per 100 parts by mass of the tablet.

6. The film-coated tablet according to claim 1, wherein the inorganic salt contained in the first film layer is a water-soluble inorganic salt.

7. The film-coated tablet according to claim 2, wherein a content of the inorganic salt in the first film layer is 20 to 55% by mass, and a content of the thickener in the second film layer is 20 to 40% by mass.

8. The film-coated tablet according to claim 2, wherein the first film layer is 2 to 6 parts by mass per 100 parts by mass of the tablet, and the second film layer is 2 to 4 parts by mass per 100 parts by mass of the tablet.

9. The film-coated tablet according to claim 2, wherein the inorganic salt contained in the first film layer is a water-soluble inorganic salt.

10. The film-coated tablet according to claim 3, wherein a content of the inorganic salt in the first film layer is 20 to 55% by mass, and a content of the thickener in the second film layer is 20 to 40% by mass.

11. The film-coated tablet according to claim 3, wherein the first film layer is 2 to 6 parts by mass per 100 parts by mass of the tablet, and the second film layer is 2 to 4 parts by mass per 100 parts by mass of the tablet.

12. The film-coated tablet according to claim 3, wherein the inorganic salt contained in the first film layer is a water-soluble inorganic salt.

13. The film-coated tablet according to claim 1, wherein a content of the first water-soluble film base in the first film layer is 30 to 80% by mass, and a content of the second water-soluble film base in the second film layer is 30 to 70% by mass.

14. The film-coated tablet according to claim 13, wherein a content of the inorganic salt in the first film layer is 20 to 55% by mass, and a content of the thickener in the second film layer is 20 to 40% by mass.

15. The film-coated tablet according to claim 2, wherein a content of the first water-soluble film base in the first film layer is 30 to 80% by mass, and a content of the second water-soluble film base in the second film layer is 30 to 70% by mass.

16. The film-coated tablet according to claim 15, wherein a content of the inorganic salt in the first film layer is 20 to 55% by mass, and a content of the thickener in the second film layer is 20 to 40% by mass.

17. The film-coated tablet according to claim 3, wherein a content of the first water-soluble film base in the first film layer is 30 to 80% by mass, and a content of the second water-soluble film base in the second film layer is 30 to 70% by mass.

18. The film-coated tablet according to claim 17, wherein a content of the inorganic salt in the first film layer is 20 to 55% by mass, and a content of the thickener in the second film layer is 20 to 40% by mass.

* * * * *